United States Patent [19]

Miura

[11] Patent Number: 5,456,880
[45] Date of Patent: Oct. 10, 1995

[54] MICROPIPET APPARATUS AND MICROMANIPULATOR

[75] Inventor: Makoto Miura, Kameoka, Japan

[73] Assignee: Shimadzu Corporation, Kyoto, Japan

[21] Appl. No.: 287,582

[22] Filed: Aug. 8, 1994

Related U.S. Application Data

[63] Continuation of Ser. No. 979,686, Nov. 20, 1992, abandoned.

[51] Int. Cl.$^6$ ........................................ B01L 3/02
[52] U.S. Cl. .................. 422/100; 73/864.11; 435/286.1; 435/286.6; 435/285.1; 435/309.1; 935/53
[58] Field of Search .................. 422/100, 99, 63–67; 436/180, 54; 73/864.11, 864.15; 935/53; 435/287

[56] References Cited

U.S. PATENT DOCUMENTS

| | | | |
|---|---|---|---|
| 3,607,082 | 9/1971 | Thiers | 23/230 |
| 3,719,087 | 3/1973 | Thiers | 73/425.6 |
| 3,982,438 | 9/1976 | Byrd | 73/864.15 |
| 4,601,551 | 7/1986 | Pettingell et al. | 350/525 |
| 4,619,899 | 10/1986 | Nikitin et al. | 435/287 |
| 4,854,355 | 8/1989 | Chazot et al. | 422/100 |
| 5,013,529 | 5/1991 | Itoh | 73/864.11 |
| 5,090,255 | 2/1992 | Kenney | 73/1 R |
| 5,106,584 | 4/1992 | Funakubo et al. | 422/63 |
| 5,143,849 | 9/1992 | Barry et al. | 422/100 |
| 5,158,748 | 10/1992 | Obi et al. | 422/63 |
| 5,225,750 | 7/1993 | Higuchi et al. | 318/280 |
| 5,343,909 | 9/1994 | Goodman | 141/242 |

OTHER PUBLICATIONS

Chambers Science and Technology Dictionary, Professor Peter M. B. Walker, Chambers Cambridge, p. 572.
McGraw-Hill Dictionary of Scientific and Technical Terms, fourth edition, Sybil P. Parker, McGraw-Hill Book Company.
Shimadzu Micromanipulator System MMS-20, Micromanipulator with Variety of Automatic Functions for Both in Biotechnology and in FTIR Spectroscopy/Surface Analysis.
Zeiss, Arbeitsplatz für Mikroinjektionen in lebende Zellen.

*Primary Examiner*—James C. Housel
*Assistant Examiner*—Jan M. Ludlow
*Attorney, Agent, or Firm*—Nikaido, Marmelstein, Murray & Oram

[57] ABSTRACT

A micromanipulator system includes a micropipet, a positive gas-pressure supply line to the micropipet, a negative gas-pressure supply line further in communication with the micropipet, and a micromanipulator for tri-dimensionally moving the micropipet. When a command for supplying either positive or negative gas pressure is issued, a controller enables either line according to a given sequence. The micromanipulator thus manipulates a small particle via the positive/negative pressure supplying and the three-dimensionnal movement or tile micropipet.

22 Claims, 5 Drawing Sheets

MICROPIPET APPARATUS AND MICROMANIPULATOR

This application is a continuation of application Ser. No. 07/979,686 filed Nov. 20, 1992 now abandoned.

BACKGROUND OF THE INVENTION

The present invention relates to a micropipet apparatus and a micromanipulator, and, more specifically, it relates to a micropipet apparatus in a micromanipulator system suitable for handling small particles such as cells.

A micromanipulator system conventionally includes a pair of micromanipulators, one of which is equipped with an injection micropipet, and the other a holding micropipet, as well as a microscope for viewing the condition of a treated cell, when, for example, a DNA solution is injected into the cell. An operator, monitoring the condition of the cell via a CRT display, controls the micropipets.

Two methods as follows have been conventionally used to vacuum-hold a cell at the end of the micropipet:

(1) Turning a screw of a micro-syringe which communicates with the micropipet so as to change the pressure inside the micropipet.

(2) Using a vacuum device which communicates with the micropipet.

With the first of these methods however, manual rotation of the screw limits precision in controlling the pressure, such that a cell held at the end of the micropipet may be sucked into it.

With the second of these methods, it is inevitable that the micropipet will occasionally draw up a cell, due to capillary action arising when the tip of the micropipet is dipped into a culture solution. Furthermore, releasing a cell held by the micropipet therein is difficult.

SUMMARY OF THE INVENTION

An object of the present invention is to improve the ability of holding and releasing a cell.

According to an aspect of the present invention, a micropipet apparatus for holding small particles such as a cell comprises a micropipet, a positive pressure line and a negative pressure line. The positive and negative pressure lines communicate with the micropipet, and enable selective supply either of a positive pressure or a negative pressure to the micropipet.

According to another aspect of the present invention, a micromanipulator for manipulating small particles such as a cell comprises a micropipet which is moved three-dimensionally. A positive pressure line and a negative pressure line are further provided. The positive and negative pressure lines communicate with the micropipet, and enable selective supply of either positive or negative pressure to the micropipet.

Small particles are manipulated with the micromanipulator by means of the positive and negative pressure supply to the micropipet and through the three-dimensional movement thereof.

The foregoing and other objects and advantages of the present invention will be more fully apparent from the following detailed description.

DESCRIPTION OF THE PREFERRED EMBODIMENTS

Figure 1:
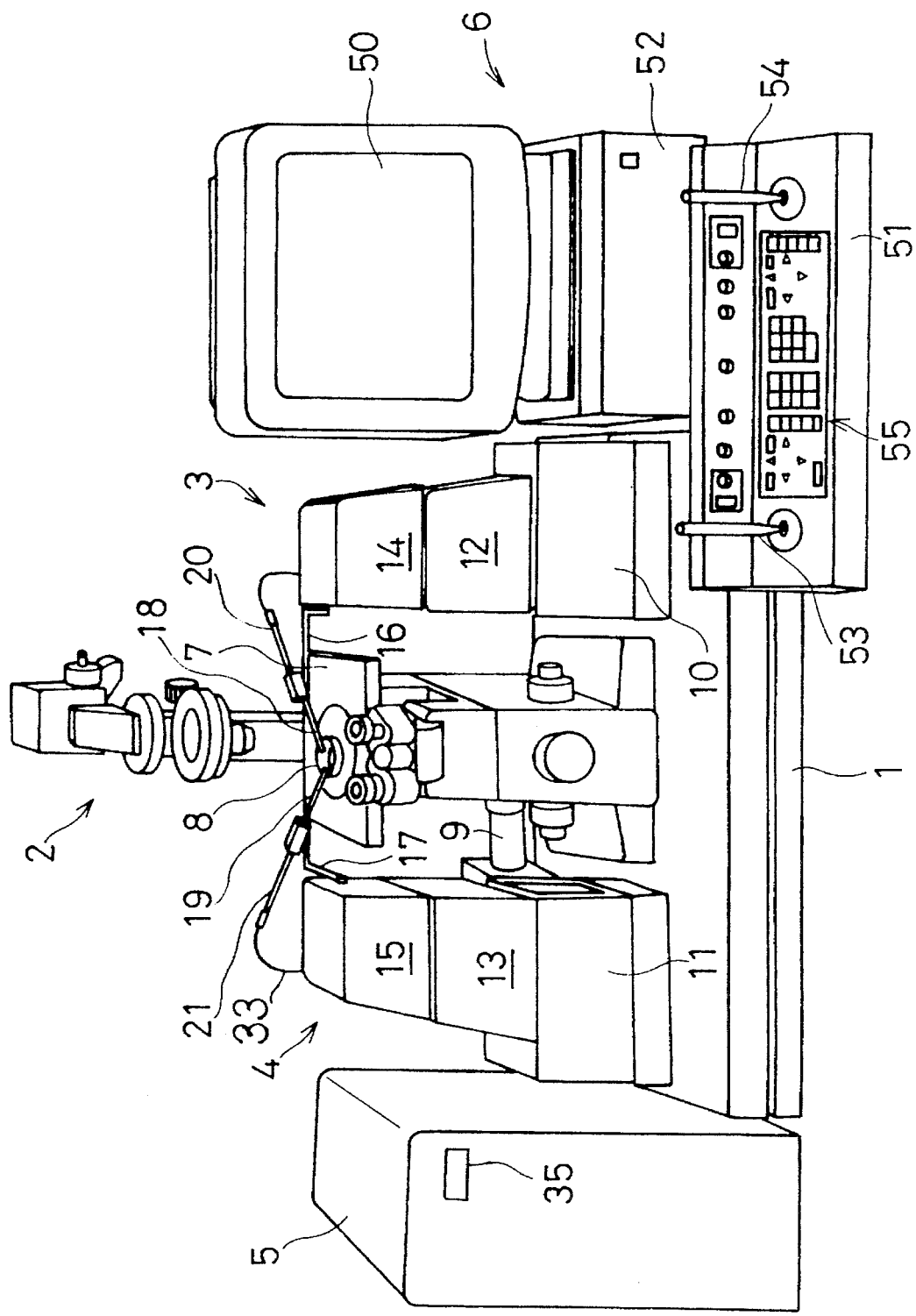
FIG. 1 is a perspective view of a micromanipulator system according to the present invention.

A micromanipulator system as shown in FIG. 1 comprises a base 1; a microscope 2 placed on the base 1; a pair of micromanipulators 3 and 4 disposed on both sides of the microscope 2; a pressure supplying device 5 for supplying positive and negative pressures to the micromanipulators 3 and 4; and a control station 6 for controlling the microscope 2 and the micromanipulators 3 and 4.

The microscope 2 has a centrally located stage 7 on which a Petri dish 8 containing a cell dispersion is placed. Disposed below the stage 7 are objective lenses (not shown) to which a television camera 9 is connected. The stage 7 is moved horizontally and vertically by a drive mechanism (not shown).

The micromanipulators 3 and 4 disposed on the base 1 comprise bottom supports 10 and 11; coarse drivers 12 and 13 on the bottom supports 10 and 11; and fine drivers 14 and 15 on the coarse drivers 12 and 13. Each of the fine drivers 14 and 15 moves an associated arm 16, 17 three-dimensionally. The one arm 16 retains an injection micropipet 18 through the tips of which injection is made, and the other arm 17 retains a holding micropipet 19 the tip of which can hold a cell. The micropipet 18 and micropipet 19 communicate with the pressure supplying device 5 through respective tubes 20 and 21.

Figure 2:
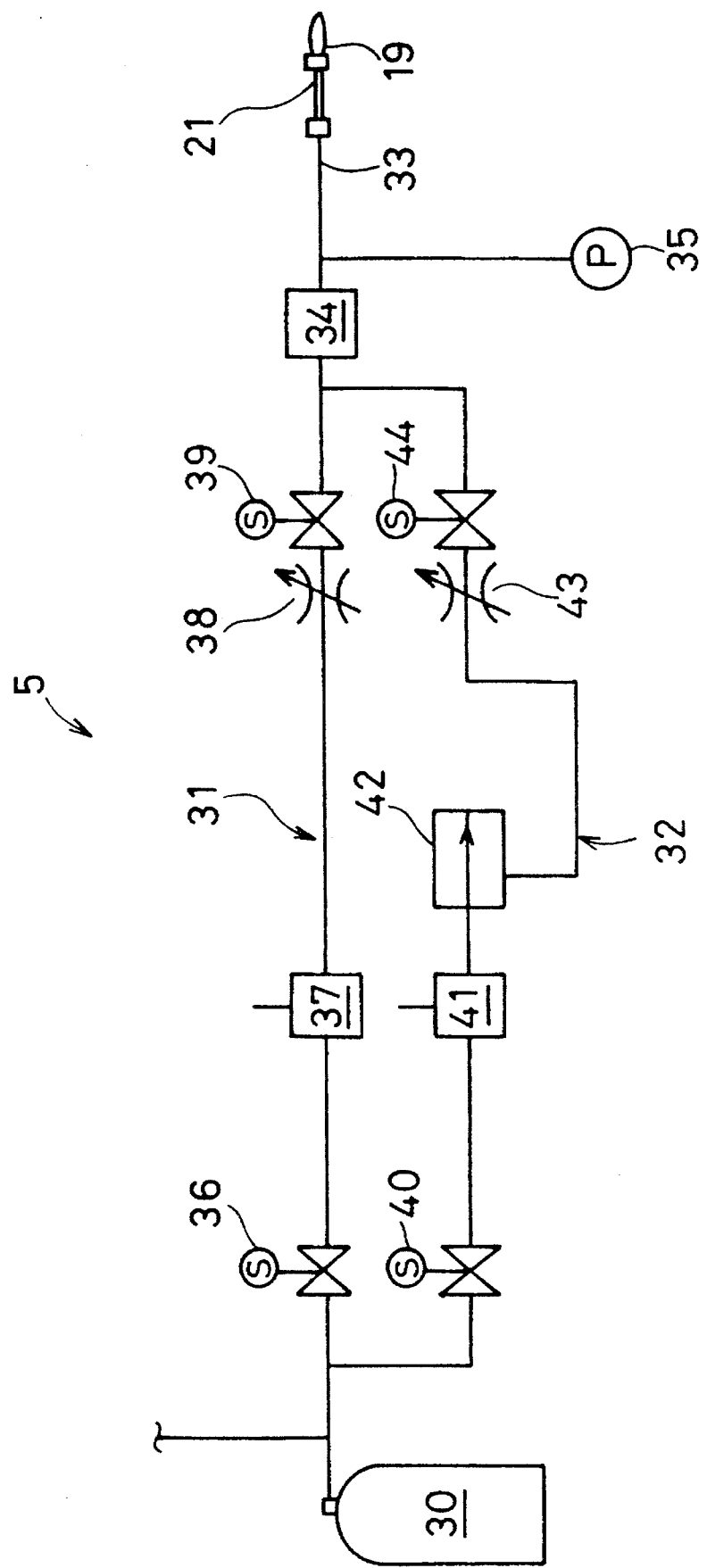
FIG. 2 is a schematic diagram showing a part or a pressure supplying device.

Referring to FIG. 2, the pressure supplying device 5 includes a mechanism supplying pressure to the micropipet 19 in addition to an associated mechanism (not shown) supplying pressure to the micropipet 18. The pressure supplying device 5 has a gas cylinder 30 containing pressurized $N_2$ gas, commonly used as a gas source in such pressure-supplying devices. Positive pressure line 31 and negative pressure line 32 of a pair, as well as other associated lines (not shown), are connected to the gas cylinder 30. The other ends of both lines 31 and 32 communicate with the micropipet 19 through the tube 21 and a common line 33. In the common line 33 are a buffer tank 34 and a pressure indicator 35.

The positive pressure line 31 includes first electromagnetic valve 36, a regulator 37, a variable restrictor 38 and a second electromagnetic valve 39, in that order from the gas cylinder 30. The variable restrictor 38 is adjusted in manufacture so that positive gas-pressure variation In response to the opening of the electromagnetic valves 36 and 39 is suitable, such that with this apparatus, problems due to capillary action at the end of the micropipet 19 are averted. The variable restrictor 38 may be a speed controller, and the regulator 37 may regulate the gas pressure within the range of between 0 and 200 kPa. The uppermost gas pressure defined by the regulator 37 is preferably in the range of 50 to 200 kPa.

The negative pressure line 32 includes a third electromagnetic valve 40, a regulator 41, an aspirator 42, a variable restrictor 43 and fourth electromagnetic valve 44, in that order from the gas cylinder 30. The gas pressure as regulated by the regulator 41 is set to be within the range of 0 to 1000 kPa. The aspirator 42 includes a venturi which effects a pressure drop according to Bernoulli's principle. When pressurized gas runs from the gas cylinder 30 through the aspirator 42, the pressure is therein reduced by the venturi, such that gas issues into the following line at lower pressure. The lowest pressure which Is developed by the aspirator 42 is set to be within the range of from 0 to −80 kPa.

The distance between the variable restrictor 38 and second electromagnetic valve 39 is preferably as short as possible, the reason being that the gas in between the variable restrictor 38 and the second electromagnetic valve 39 becomes compressed when the electromagnetic valve 39 is closed, and the compressed gas released upon opening it rapidly increases the pressure inside the micropipet 19. Accordingly, the amount of gas in between the variable restrictor 38 and electromagnetic valve 39 should be as small as possible.

The distance between the variable restrictor 43 and the fourth electromagnetic valve 44 should also be as short as possible, for the reason that the pressure of the gas in between the variable restrictor 43 and the electromagnetic valve 44 is lowered by the aspirator 42 when the electromagnetic valve 44 is closed, and the negatively-pressurized gas suddenly lowers the pressure inside the micropipet 19 just after the electromagnetic valve 44 is opened. Sudden increase or decrease of the pressure inside the micropipet 19 may blow off cells therefrom or draw cells thereinto.

To secure a solution to the above problem, the buffer tank 34 is provided. The buffer tank 34 functions as an accumulator to absorb sudden changes in pressure caused by opening of the electromagnetic valves 39 and 44. The volume of the buffer tank 34 is within the range or 50 to 1000 cm$^3$, more preferably 90 to 500 cm$^3$. The tank volume should be determined so that the pressure change when opening the electromagnetic valves 39 or 44 is ½ kPa or less, more preferably ⅕ kPa or less, and optimally ¹⁄₁₀ kPa or less.

Referring back to FIG. 1, the control station 6 comprises a monitor 50, an operation panel 51 and a control unit 52. The chief component of the monitor 50 is a cathode ray tube. The operation panel 51 includes a pair of joysticks 53 and 54 for control of the micromanipulators 3 and 4, and a keyboard 55 containing assorted keys, in particular, a "DRAW" key 56 and a "RELS" key 57.

Figure 3:
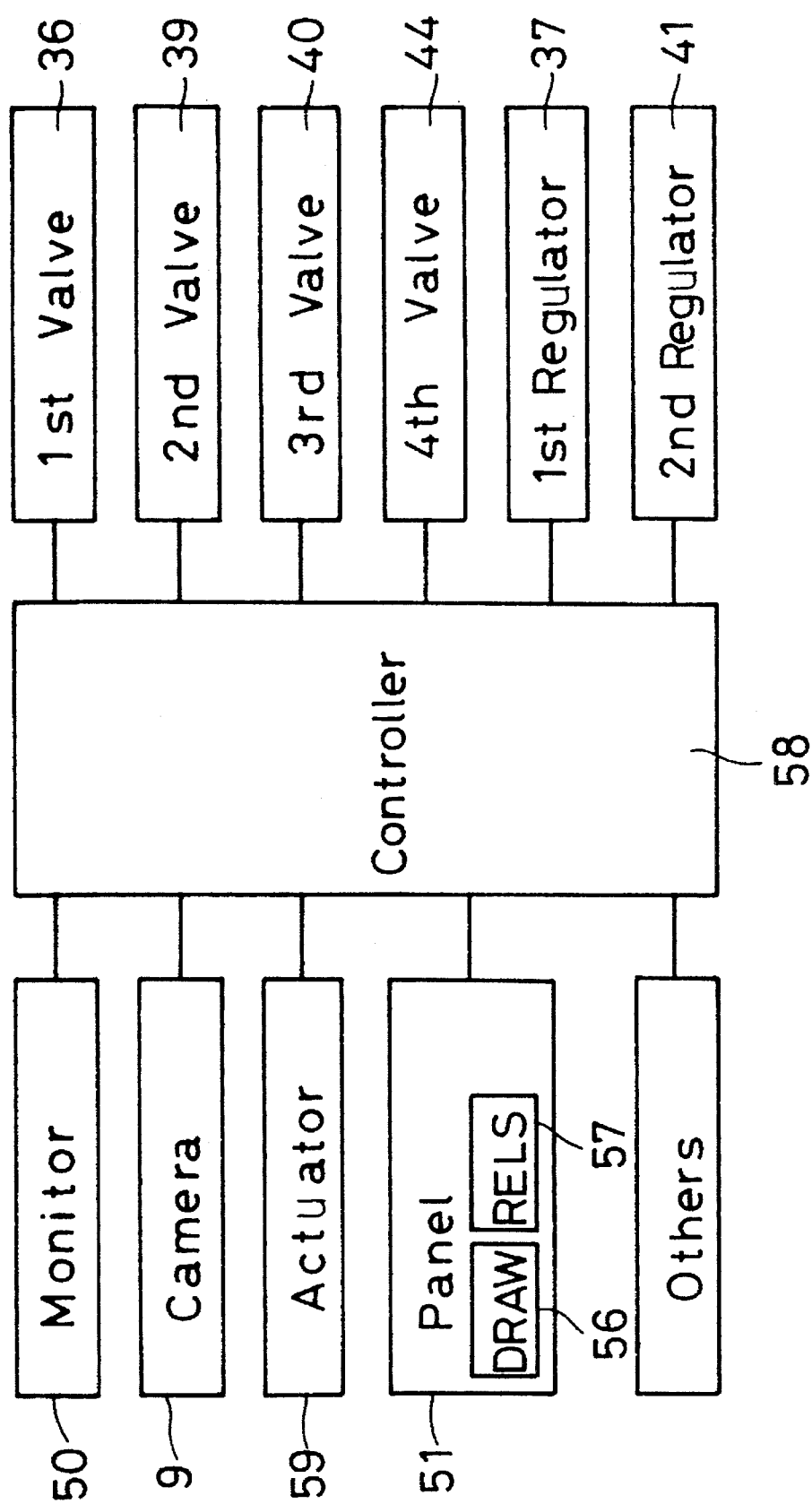
FIG. 3 is a schematic block diagram of a control unit.

The control unit 52 includes a controller 58, illustrated by FIG. 3, which contains CPUs, RAMs and ROMs. The controller 58 is electronically connected to the monitor 50, the television camera 9, the operation panel 51, and other associated components, including an actuator 59 for the micromanipulators 3 and 4. Furthermore, the controller 58 is electronically connected to the first through fourth electromagnetic valves 36, 39, 40 and 44, respectively, and the first and second regulators 37 and 41.

Figure 4:
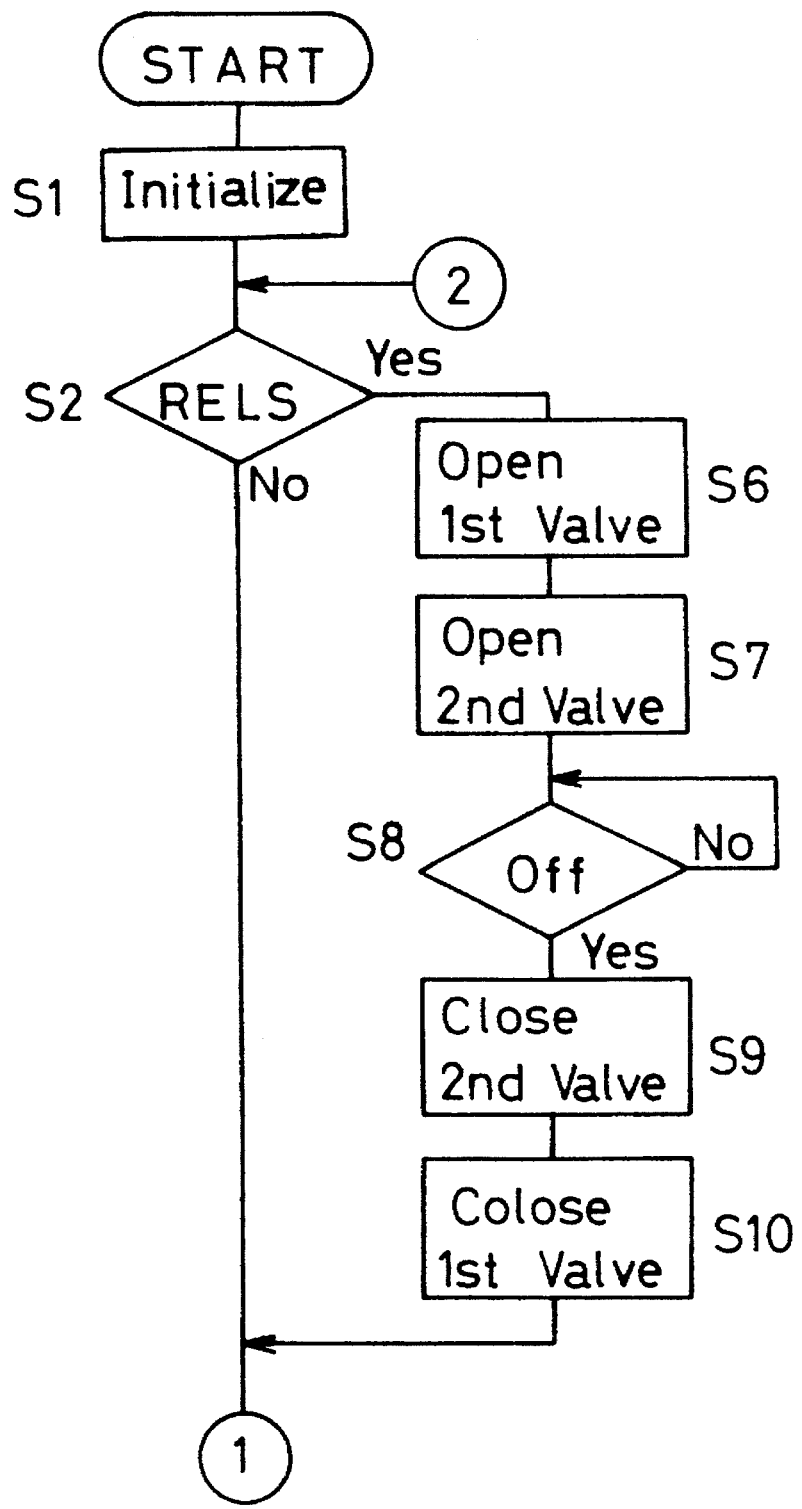
FIGS. 4 and 5 are flow charts illustrating the micromanipulator system control process.
Figure 5:
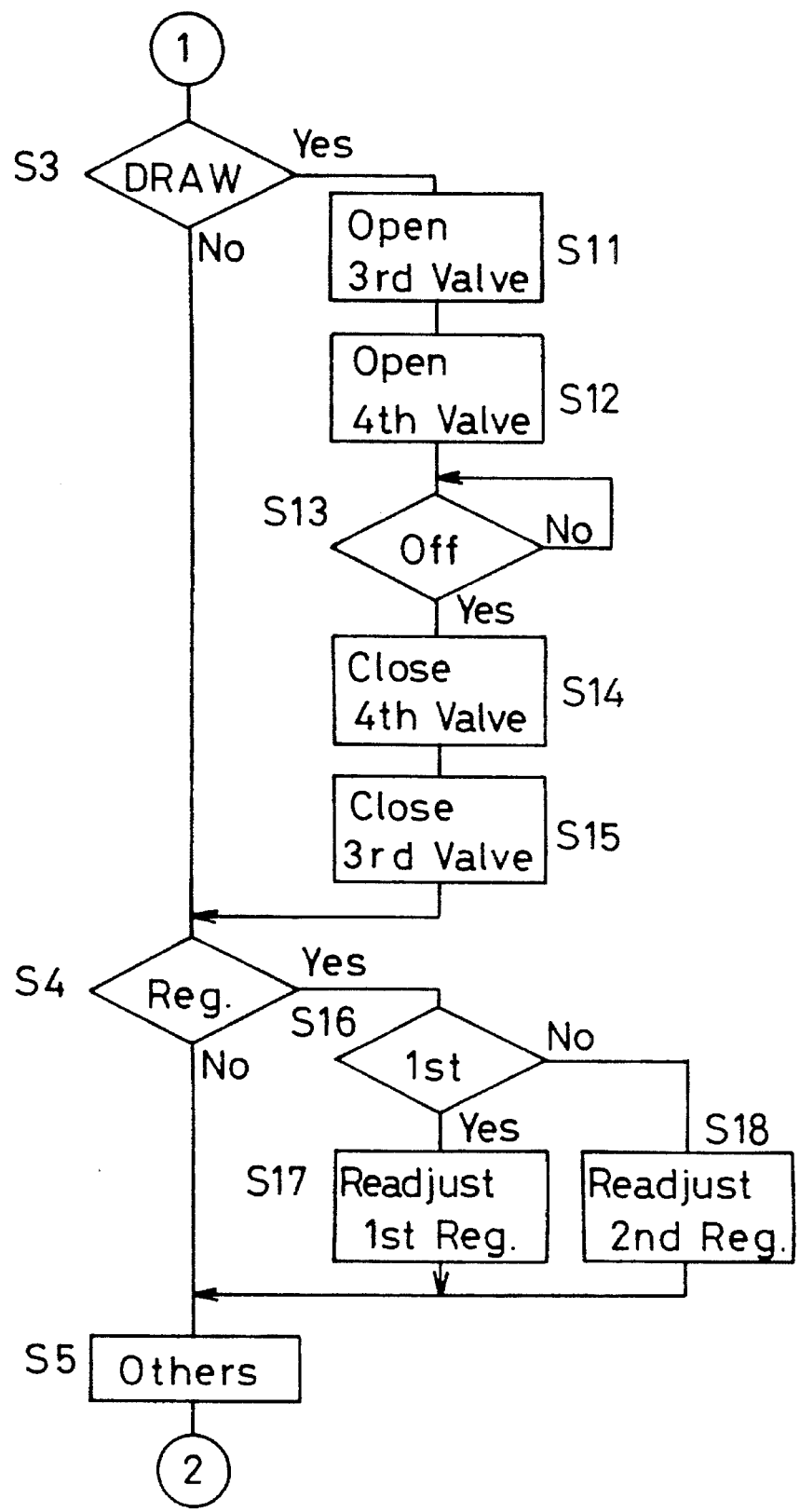

Operation of the micromanipulator system will now be described, referring to the program Illustrated by the flowcharts diagramed in FIGS. 4 and 5.

At step S1, an initialization is executed in which the monitor 50 displays an initial menu, and the microscope 2 and micromanipulators 3 and 4 are positioned into an initial state.

After the initialization, it is determined at step S2 whether the "RELS" key 57 has been pressed, i.e., whether a cell-releasing operation has been commanded by the operator. It is then determined, at step S3 of FIG. 5, whether the "DRAW" key 56 has been pressed, i.e., whether a cell-holding operation has been commanded by the operator.

At step S4, it is determined whether readjustment of the regulators 37 and 41 has been commanded by the operator through pressing the corresponding keys on the keyboard 55.

At step S5, other successive processes are carried out in accordance with commands made by the operator. The processes executable at step S5 include, inter alia, a process changing the monitor 50 display, a process manipulating the micropipet 18 and the micropipet 19, and a process changing the magnification ratio of the microscope 2. After the execution of step S5, the program returns to step S2 of FIG. 4.

Wherein the "RELS" key 57 has been pressed, step S6 is executed, at which the first electromagnetic valve 36 goes open. This results in an increase of gas pressure in the positive pressure line 31. The gas pressure is regulated by the regulator 37. Then, at step S7, the second electromagnetic valve 39 goes open, whereby the pressure In the micropipet 19 is gradually increased.

The program remains at step S8, wherein both valves 36 and 39 are kept open and the gas pressure to the micropipet 19 is kept high, until the "RELS" key 57 is released.

Accordingly, by pressing the "RELS" key 57, a cell is released from the tip of the micropipet 19, wherein effects due to capillarity are averted, since the regulator 37 and the determined which of the first and second regulators 37 and 41 are to be readjusted. If it has been commanded to readjust the first regulator 37, step S17 is executed, at which the first regulator 37 is readjusted In accordance with the operator's instruction. Meanwhile, if it has been commanded to readjust the second regulator 41, step S18 is executed, at which the second regulator 41 is readjusted in accordance with the operator's instruction. After the execution of either step S17 or step S18, the program returns to the main routine.

According to the aforementioned embodiment, a cell in the Petri dish 8 can be gently held by the micropipet 19 in cooperation with the pressure supplying device 5 shown in FIG. 2, wherein the cell take-up and release operations may be carried out with ease by the operator and problems due to capillarity are averted. By adjusting the regulators 37 and 41 and the variable restrictors 38 and 43, the operator can easily change such functional characteristics of the micropipet 19 as pressure variation and the maximum and minimum pressures.

MODIFICATIONS

The regulators 87 and 41 may be adjusted manually by the operator instead of being adjusted by the controller 88.

Wherein there is no necessity to change the speed of pressure increase and decrease the regulators 87 and 41 could be omitted. variable restrictor 38 are adjusted so as to achieve a balance between the pressure both inside and outside the micropipet 19.

After releasing the "RELS" key 57, step S9 is executed, at which the second electromagnetic valve 39 is first closed, and then the first electromagnetic valve 36 is closed. After the execution of step S10, the program returns to the main routine.

Wherein the "DRAW" key 56 has been pressed, step S11 is executed, at which the third electromagnetic valve 40 goes open. This results in an increase of gas pressure in the negative pressure line 32. The gas pressure is regulated by the regulator 41. When the compressed gas from the gas cylinder 30 has thus gone through the aspirator 42, the gas pressure just before the fourth electromagnetic valve 44 will be minimal, creating a negative pressure. Then at step S12, the fourth electromagnetic valve goes open, whereby the pressure inside the micropipet 19 is gradually decreased. Accordingly, the micropipet 19 can gently hold a cell at its end.

The program remains at step S13, wherein both the valves 41 and 44 are kept open and the gas pressure of the micropipet 19 is kept low, until the "DRAW" key 56 is released.

The rate of applied pressure variation inside the micropipet 19 can be controlled and adjusted by changing the state of the regulators 37 and 41. The operator can effect this by pressing corresponding keys on the keyboard 55, wherein the program runs from step S4 in FIG. 5 to step S16. At step S16, it is Various details of the invention may be changed without departing from its spirit nor its scope. Furthermore, the foregoing description of the embodiments according to the present Invention is provided for the purpose of illustration only, and not for the purpose of limiting the invention as defined by the appended claims and their equivalents.

What is claimed is:

1. A micropipet apparatus for holding a microscopic particle, comprising:
   a micromanipulator for micromanipulating a micropipet disposed thereupon;
   positive pressure supplying means in communication with said micropipet for supplying positive pressure thereto, said positive pressure supplying means including a first valve and a first variable restrictor;
   negative pressure supplying means in communication with said micropipet for supplying negative pressure thereto;
   selecting means for selecting one of said positive and negative pressure-supplying means; and
   a gas supply means in gas flow communication with said positive and negative pressure supplying means, said gas supply means supplying gas pressure to said positive and negative pressure supplying means, said positive and negative pressure being controlled such that said micropipet can manipulate microscopic particles.

2. An apparatus according to claim 1, wherein said gas supply means is a gas supply cylinder containing a pressurized gas.

3. A micromanipulator system comprising:
   a micromanipulator for micromanipulating a micropipet disposed thereupon said micromanipulator for tri-dimensionally moving said micropipet, said micromanipulator including a coarse driver and a fine driver, said fine driver disposed on said coarse driver and having an arm holding said micropipet;
   positive pressure supplying means in communication with said micropipet for supplying a positive pressure thereto;
   negative pressure supplying means in communication with said micropipet for supplying a negative pressure thereto;
   means for selecting one of said positive and negative pressure supplying means;
   a microscope disposed adjacent said micropipet; and
   a gas supply cylinder in gas flow communication with said positive and negative pressure supplying means, said gas supply cylinder containing a pressurized gas therein and supplying said pressurized gas to said positive and negative pressure supplying means, said positive and negative pressure being controlled such that said micropipet can manipulate microscopic particles.

4. An apparatus according to claim 3, wherein said positive pressure supplying means includes a regulator which regulates gas pressure in the positive pressure-supplying means to be between 0 and 200 kPa.

5. An apparatus according to claim 3, wherein said negative pressure-supplying means includes a first valve, a regulator, an aspirator, a variable restrictor and a second valve, in that order, which are in gas flow communication with said gas cylinder.

6. An apparatus according to claim 5, wherein said aspirator includes a venturi functioning according to Bernoulli's principle to effect pressure reduction.

7. An apparatus according to claim 6, wherein a lowest pressure effected within said aspirator is within the range of 0 to −80 kPa.

8. An apparatus according to claim 5, wherein said second regulator regulates gas pressure In the negative pressure-supplying means to be within the range of 0 to 1000 kPa.

9. An apparatus according to claim 5, wherein said selecting means includes a controller electronically connected to said first and second valves.

10. An apparatus according to claim 9, wherein said controller is further electronically connected to said regulator.

11. An apparatus according to claim 10, wherein said selecting means further includes a keyboard electronically connected to said controller, by means of which commands for said positive and negative pressure-supplying are issued.

12. An apparatus according to claim 11, wherein said controller controls said first valve to open, and subsequently said second valve to open to supply negative pressure.

13. A micromanipulator system according to claim 3, wherein said positive pressure supplying means includes a first valve, a first regulator, a first variable restrictor, and a second valve, in gas flow communication with said gas supply cylinder in sequential order.

14. An apparatus according to claim 13, wherein said controller controls said first valve to open, and subsequently said second valve to open to supply positive pressure.

15. An apparatus according to claim 3, further comprising a buffer tank in flow communication with said micropipet for absorbing sudden pressure changes inside said micropipet arising from selecting of either of said positive and negative pressure-supplying means.

16. An apparatus according to claim 15, wherein the volume of said buffer tank is within the range of 50 to 1000 cm$^3$.

17. An apparatus according to claim 15, wherein the volume of said buffer tank is such that said pressure changes are constrained to be within the range of 0 to ½ kPa.

18. A micropipet apparatus, comprising:
   a micromanipulator having a base;
   at least a first driver mounted to said base;
   a micropipet mounted to said first driver, said first driver configured for micrometer movement of said first micropipet;
   an operation panel connected to said micromanipulator for controlling movement of said driver;
   a positive pressure supplying means in communication with said micropipet for supplying positive pressure thereto;
   negative pressure supplying means in communication with said micropipet for supplying negative pressure thereto;
   a gas supply means in gas flow communication with said positive and negative pressure supplying means, said gas supply means supplying gas pressure to said positive and negative pressure supplying means, said positive and negative pressure being controlled such that said micropipet can manipulate microscopic particles; and a controller connected to said operation panel and said micromanipulator having a selecting means for selectively connecting one of said positive and negative pressure-supplying means to said micropipet.

19. A micropipet apparatus as set forth in claim 18, further comprising:

a second driver mounted to said first driver configured for micrometer movement of said micropipet, said micropipet mounted to said second driver such that said first driver provides coarse micrometer movement of said micropipet and said second driver provides fine micrometer movement of said micropipet.

20. A micropipet apparatus as set forth in claim 19, further comprising:

a stage disposed adjacent said micropipet, said stage being configured to receive a Petri dish;

a camera mounted to said base, said camera being focusable on said Petri dish; and a monitor connected to said camera for displaying images from said camera.

21. A micropipet apparatus as set forth in claim 19, further comprising:

a third driver mounted to said base, a fourth driver mounted to said third driver and a second micropipet mounted to said third driver, said third and fourth drivers configured for micrometer movement of said micropipet, wherein said operation panel comprises at least one joystick control for control of movement of said first micropipet and a second joystick control for control of movement of said second micropipet.

22. A micropipet apparatus as set forth in claim 18 wherein said operation panel comprises at least one joystick control for control of movement of said micropipet.

* * * * *